US012569539B2

(12) United States Patent
Takei et al.

(10) Patent No.: US 12,569,539 B2
(45) Date of Patent: Mar. 10, 2026

(54) ADIPOCYTES OVER-EXPRESSING FFAR4 AND USE THEREOF

(71) Applicants: NUMT INC., Kawasaki (JP); TOHO UNIVERSITY, Tokyo (JP)

(72) Inventors: Yoshinori Takei, Tokyo (JP); Akira Hirasawa, Kyoto (JP)

(73) Assignees: NUMT INC., Kawasaki (JP); TOHO UNIVERSITY, Tokyo (JP)

( * ) Notice: Subject to any disclaimer, the term of this patent is extended or adjusted under 35 U.S.C. 154(b) by 635 days.

(21) Appl. No.: 17/928,092

(22) PCT Filed: May 26, 2021

(86) PCT No.: PCT/JP2021/020097
§ 371 (c)(1),
(2) Date: Nov. 28, 2022

(87) PCT Pub. No.: WO2021/241659
PCT Pub. Date: Dec. 2, 2021

(65) Prior Publication Data
US 2023/0210945 A1     Jul. 6, 2023

(30) Foreign Application Priority Data
May 29, 2020     (JP) ................................. 2020-094495

(51) Int. Cl.
| | |
|---|---|
| *A61K 38/17* | (2006.01) |
| *A61K 35/35* | (2015.01) |
| *A61P 3/10* | (2006.01) |
| *A61P 25/28* | (2006.01) |
| *C12N 5/077* | (2010.01) |
| *C12N 15/86* | (2006.01) |

(52) U.S. Cl.
CPC ............ *A61K 38/177* (2013.01); *A61K 35/35* (2013.01); *A61P 3/10* (2018.01); *A61P 25/28* (2018.01); *C12N 5/0653* (2013.01); *C12N 15/86* (2013.01); *C12N 2506/1384* (2013.01); *C12N 2510/00* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2006/0121008 A1 | 6/2006 | Ito et al. |
| 2008/0004227 A1* | 1/2008 | Hirasawa .................. A61P 3/10 |
| | | 435/320.1 |
| 2010/0274022 A1 | 10/2010 | Tsujimoto et al. |
| 2020/0270640 A1* | 8/2020 | Jiménez Cenzano ........................ |
| | | A61K 48/0058 |

FOREIGN PATENT DOCUMENTS

| | | |
|---|---|---|
| CN | 106086072 A | 11/2016 |
| CN | 109420175 A | 3/2019 |
| JP | 2008001690 A | 1/2008 |
| JP | 2012520240 A | 9/2012 |
| JP | 2016214135 A | 12/2016 |
| JP | 2019137681 A | 8/2019 |
| WO | 03106663 A1 | 12/2003 |
| WO | 2005083070 A1 | 9/2005 |
| WO | 2007134613 A1 | 11/2007 |
| WO | 2008139879 A1 | 11/2008 |
| WO | 2009038204 A1 | 3/2009 |
| WO | 2009125804 A1 | 10/2009 |
| WO | 2010104195 A1 | 9/2010 |

OTHER PUBLICATIONS

Oh DY, Talukdar S, Bae EJ, Imamura T, Morinaga H, Fan W, Li P, Lu WJ, Watkins SM, Olefsky JM. GPR120 is an omega-3 fatty acid receptor mediating potent anti-inflammatory and insulin-sensitizing effects. Cell. Sep. 3, 2010;142(5):687-98. (Year: 2010).*
Addgene via Kroeze WK, Sassano MF, Huang XP, Lansu K, McCorvy JD, Giguere PM, Sciaky N, Roth BL.Presto-Tango as an open-source resource for interrogation of the druggable human GPCRome. Nat Struct Mol Biol. May 2015;22(5):362-9. https://www.addgene.org/browse/article/10377/. (Year: 2015).*
Alexander SP, Christopoulos A, Davenport AP, Kelly E, Marrion NV, Peters JA, Faccenda E, Harding SD, Pawson AJ, Sharman JL, Southan C, Davies JA; CGTP Collaborators. The Concise Guide to Pharmacology 2017/18: G protein-coupled receptors. Br J Pharmacol. Dec. 2017;174 Suppl 1(Suppl Suppl 1):S17-S129. (Year: 2017).*
Akkerman, Sven et al., "Object recognition testing: Methodological considerations on exploration and discrimination measures", Behav Brain Res, 2012, pp. 335-347, vol. 232.
Antunes, M. et al., "The novel object recognition memory: neurobiology, test procedure, and its modifications", Cogn Process, 2012, pp. 93-110, vol. 13.
Hara, Takafumi et al., "Free Fatty Acid Receptors and Their Role in Regulation of Energy Metabolism", Rev Physiol Biochem Pharmacol, 2013, pp. 77-116, vol. 164.
Hirasawa, Akira et al., "Free fatty acids regulate gut incretin glucagon-like peptide-1 secretion through GPR120", Nature Medicine, Jan. 2005, pp. 90-94, vol. 11, No. 1.
Ichimura, Atsuhiko et al., "Dysfunction of lipid sensor GPR120 leads to obesity in both mouse and human", Nature, Mar. 15, 2012, pp. 350-354, vol. 483.
Ichimura, Atsuhiko, "Analyses of regulatory mechanisms of energy homeostatis via free fatty acids receptors", Jun. 11, 2018, https://kaken.nii.ac.jp/en/file/KAKENHI-PROJECT-15H06652/15H05652seika.pdf.
Leger, Marianne et al., "Object recognition test in mice", Nature Protocols, 2013, pp. 2531-2537, vol. 8, No. 12.

(Continued)

*Primary Examiner* — Christopher M Babic
*Assistant Examiner* — Alyssa G Weston
(74) *Attorney, Agent, or Firm* — The Webb Law Firm

(57) ABSTRACT

Provided herein is a method for treating and/or preventing various diseases including a decrease in glucose tolerance and a decrease in cognitive ability associated with aging with adipocytes over-expressing FFAR4 and a transplant composition including the adipocytes.

7 Claims, 14 Drawing Sheets

(56)           References Cited

OTHER PUBLICATIONS

Milligan, Graeme et al., "FFA4/GPR120: Pharmacology and Thera-peutic Opportunities", Trends in Pharmacological Sciences, Sep. 2017, pp. 809-821, vol. 38, No. 9.

Sun, Qi et al., "Structure-Activity Relationships of GPR120 Agonists Based on a Docking Simulation", Mol Pharmacol, 2010, pp. 804-810, vol. 78, No. 5.

BAE In-Seon, et al., "PPARγ-mediated G-protein coupled receptor 120 signaling pathway promotes transcriptional activation of miR-143 in adipocytes", Gene, May 8, 2017, pp. 64-69, vol. 626.

Im, Dong-Soon, "FFA4 (GPR120) as a fatty acid sensor involved in appetite control, insulin sensitivity and inflammation regulation", Molecular Aspects of Medicine, Oct. 2017, pp. 1-17.

Song, Tongxing, et al., "GPR120: a critical role in adipogenesis, inflammation, and energy metabolism in adipose tissue", Cell. Mol. Life Sci., 2017, pp. 2723-2733, vol. 74, No. 15.

* cited by examiner 6 hours resting

Familiar object    Novel object

ADIPOCYTES OVER-EXPRESSING FFAR4 AND USE THEREOF

CROSS-REFERENCE TO RELATED APPLICATIONS

This application is the United States national phase of International Application No. PCT/JP2021/020097 filed May 26, 2021, and claims priority to Japanese Patent Application No. 2020-094495 filed May 29, 2020, the disclosures of which are hereby incorporated by reference in their entirety.

BACKGROUND OF THE INVENTION

Field of the Invention

The present invention relates to adipocytes over-expressing FFAR4 useful in treating and/or preventing various diseases, a transplant composition comprising the adipocytes, and a method for treating and/or preventing various diseases of animals and human using the transplant composition. It is assumed that the target diseases in the present invention include, for example, a decrease in glucose tolerance and a decrease in cognitive functions associated with aging.

Description of Related Art

It is known that the glucose tolerances decrease along with aging, and elderly people are likely to have blood sugar levels 2 hours after meals of exceeding 140 mg/dL (postprandial hyperglycemia), and risks of diabetes increase. It is considered that to prevent diabetes of elderly people, therapies are effective which suppress an increase in blood sugar level after meal, in other words, improve a decrease in glucose tolerance associated with aging. However, the existing antidiabetic agents involve concerns of side effects such as hypoglycemia and no safe therapeutic methods have been established currently.

The G protein-coupled receptors (GPCRs) are receptors having molecular structures characteristic to penetrate a cell membrane seven times, and target molecules of therapeutic drugs against many diseases such as hypertension, arrhythmia, angina, asthma, and peptic ulcer belong to this gene family. For this reason, GPCRs are attracting attention as drug target molecules. GPCRs are extracellularly activated by a specific ligand to transfer the information to the G protein in the cells, generating a bioactivity. It is considered that by binding to the specific ligands, the above-described characteristic molecular structure of the GPCRs significantly change to cause activation of the G protein.

It has been found that FFAR4 (which had been referred to as GPR120 before the name was defined, and which is the same as the amino acid sequence registered as NP_859529 in the GenBank), which is one of GPCRs, is a free fatty acid receptor that activates intracellular communications using free fatty acids (particularly, ω-3 fatty acids such as DHA and EPA, which are essential fatty acids), which are nutrients important as energy sources, as ligands. As the physiological function of FFAR4, a mechanism of promoting secretion of ininsulinotropic peptide hormone GLP-1 from the intestinal tract by means of the free fatty acid stimulation has been revealed (Hirasawa, A. et al. Nat. Med. 11, 90-94, 2005 (NPL 1)). In addition, for FFAR4, it has also been confirmed from an interaction analysis method of a ligand and a receptor using a fluorescent ligand and a flow cytometer in combination that FFAR4 interacts with a long-chain fatty acid (Sun, Q et al. Mol. Pharmacol. 78, 804-810, 2010 (NPL 2)). Furthermore, phenotypes such as hypertrophy of adipocytes, an increase in weight of adipose tissue, an increase in body weight, fatty liver, and abnormal glucose tolerance were observed in knockout mice of FFAR4. This phenomenon is considered to be caused by a suppression of differentiation by adipose tissues and a decrease in fatty acid synthesis (Ichimura, A. et al. Nature 483,350-354, 2012 (NPL 3)). As described above, it has been indicated that FFAR4 is significantly involved in dietary obesity as a sensor of fatty acids, and it has been expected that preventive and therapeutic drugs for dietary obesities targeting FFAR4 are applied and developed (Hara, T. et al. Rev Physiol Biochem Pharmacol. 164, 77-116, 2013; Milligan, G. et al. Trends Pharmacol Sci. 38, 809-821, 2017. (NPL 4, 5)).

The development of application to preventive and therapeutic drugs targeting FFAR4 has been directed so far to searching for a compound having a FFAR4 agonistic activity, and studies have been conducted to search for a compound that has a FFAR4 agonistic activity and is useful in treatment and/or preventive drugs of diabetes, obesity, and hyperlipidemia (Japanese Patent Laid-Open No. 2012-520240 (PTL 1), Japanese Patent Laid-Open No. 2008-001690 (PTL 2), and International Publication No. 2005/083070 (PTL 3)). In addition, although cells in which genes encoding FFAR4 are introduced have been constructed, these are for screening of ligands and analyzing the activities (Japanese Patent Laid-Open No. 2016-214135 (PTL 4), Published Japanese Translation of PCT International Application No. 2012-520240 (PTL 1), and Japanese Patent Laid-Open No. 2008-001690 (PTL 2)), and there has been no attempt to use cells in which genes encoding FFAR4 are introduced for treatment. In addition, in such objects of analysis as well, FFAR4 analysis in adipocytes is conducted by using those obtained by differentiation-inducing cultured cells 3T3-L1 derived from mice into adipocytes. However, the methods are those using differentiation-induction by adding an agonists of FFAR4, inhibition of FFAR4 expression using siRNA and the like, and the like, and no case of adipocytes hyper-expressing (over-expressing) FFAR4 is known.

International Publication No. 2003/106663 (PTL 5) discloses an ex vivo gene therapy method using adipocytes in which exogenous genes are introduced. However, this invention is such that transplanted adipocytes produce in vivo proteins (hormones such as insulin and GLP-1) encoded by the introduced exogenous gene like a production plant to secrete the proteins out of the cells, and does not assume at all transplantation of adipocytes in which a receptor penetrating a cell membrane is expressed.

The Specification of International Publication No. 2005/083070 (PTL 3) describes an invention relating to a composition for lowering a blood sugar level, comprising a "GT01 polypeptide". However, the "GT01 polypeptide" in this invention means a G protein-coupled receptor that is distributed on the surfaces of intestinal endocrine cells or intestinal endocrine cell lines to transfer a signal for secretion of GLP-1 into cells by coupling of the ligands, and does not intend to express on the surfaces of adipocytes. Note that there is no report that FFAR4 promotes secretion of GLP-1 in adipocytes. In addition, although PTL 3 mentions an ex vivo treatment as a gene treatment composition, but fails to disclose any specific gene introduction technique, and does not mention at all gene introduction into adipocytes, or adipose stem cells or adipose precursor cells.

Moreover, the maintenance and improvement of cognitive functions have been demanded in a wide range of generations from young people to old people, and particularly the maintenance and improvement of memory power, thinking power, and judging power are important in conducting daily lives, which also leads to prevention of decreases in cognitive functions associated with aging, extension of healthspan, and suppression of a decrease in quality of life, in old people.

Various propositions have been made in terms of compositions for maintaining or improving cognitive functions. For example, various compositions such as various compounds and natural products including medium-chain triglyceride, lactoferrin, lactoferrin hydrolysate, docosahexaenoic acid, white-rind cheese or pulverized products thereof, specific amino acids, and lipopolysaccharide, have been studied. However, there is no report that associates FFAR4 or adipocytes expressing FFAR4 with cognitive functions.

In addition, a regenerative medicine utilizing mesenchymal stem cells to treat or improve damaged brain functions is also known (Japanese Patent Laid-Open No. 2019-137681 (PTL 6)). However, this utilizes the characteristic of mesenchymal stem cells that the mesenchymal stem cells differentiate into cells such as nerve cells, but does not indicate the relevance between FFAR4 and cognitive functions.

CITATION LIST

Patent Literature

PTL 1: Japanese Patent Laid-Open No. 2012-520240
PTL 2: Japanese Patent Laid-Open No. 2008-001690
PTL 3: International Publication No. 2005/083070
PTL 4: Japanese Patent Laid-Open No. 2016-214135
PTL 5: International Publication No. 2003/106663
PTL 6: Japanese Patent Laid-Open No. 2019-137681

Non Patent Literature

NPL 1: Hirasawa, A. et al. Nat. Med. 11, 90-94, 2005
NPL 2: Sun Q et al. Mol. Pharmacol. 78, 804-810, 2010
NPL 3: Ichimura, A. et al. Nature 483,350-354, 2012
NPL 4: Hara, T. et al. Rev. Physiol. Biochem. Pharmacol. 164, 77-116, 2013
NPL 5: Milligan, G. et al. Trend Pharmacol. Sci. 38, 809-821, 2017

SUMMARY OF INVENTION

Technical Problem

The present invention provides a novel method for improving or preventing various diseases including a decrease in glucose tolerance and a decrease in cognitive functions associated with aging.

Solution to Problem

The present inventors have found that a decreased glucose tolerance due to aging is improved by transplanting adipocytes over-expressing FFAR4, that is, adipocytes modified by introducing a gene encoding FFAR4 into the adipocytes to express FFAR4 into an aged animal. This means the adipocytes over-expressing FFAR4 can be a therapeutic method for improving a glucose tolerance decreased in association with aging.

In addition, it has also been found that a decrease in cognitive ability associated with aging is improved by transplanting adipocytes over-expressing FFAR4 into an aged animal. There has been no dissertation reporting the relation between FFAR4 and cognitive ability, and this result is completely surprising.

In this way, there is a possibility that transplanting adipocytes over-expressing FFAR4 into an aged animal can be used for treating or preventing not only a decrease in glucose tolerance or a decrease in cognitive ability of animals and humans associated with aging but also various diseases.

In addition, the present invention relates to a transplant composition comprising adipocytes over-expressing FFAR4, and the present invention further relates to methods for treating and/or preventing various diseases, particularly preventing or improving a decrease in glucose tolerance associated with aging and preventing or improving a decrease in cognitive ability associated with aging, as well as the methods comprising: transplanting a transplant composition comprising adipocytes over-expressing FFAR4 into a human or an animal.

Moreover, according to one aspect, the present invention relates to a method comprising: causing an adipose tissue-derived stem cell collected from a human or an animal to over-express FFAR4 through gene modification; differentiating and inducing the adipose tissue-derived stem cell into adipocytes; and autotransplanting the adipocytes.

Examples of specific aspects of the present invention will be described below.

(1) Adipocytes modified to express FFAR4 by introducing a gene encoding FFAR4 into the adipocytes.

(2) The adipocytes according to item 1, in which the adipocytes are obtained by introducing FFAR4 gene into an adipose stem cell or an adipose precursor cell derived from an adipose tissue to forcibly express FFAR4, and then inducing differentiation thereto.

(3) The adipocytes according to item 2, in which adipocytes are obtained by a method including:

a creating a chimeric gene in which human FFAR4 cDNA (NM_181745) is placed downstream of an appropriate promoter sequence;

b introducing the chimeric gene into the adipose stem cell or the adipose precursor cell by incorporating the chimeric gene in a virus or the like; and c differentiating the adipose stem cell or the adipose precursor cell in which the chimeric gene has been introduced to adipocytes.

(4) The adipocytes according to item 1, in which the adipocytes are adipocytes isolated from an adipose tissue of a transgenic mouse in which a gene encoding FFAR4 has been introduced.

(5) The adipocytes according to item 1, for treating and/or preventing various diseases.

(6) The adipocytes according to item 5, in which the diseases are a decrease in glucose tolerance associated with aging.

(7) The adipocytes according to item 5, in which the diseases are a decrease in cognitive ability associated with aging.

(8) A method for producing the adipocytes according to item 2, including:

a creating a chimeric gene in which human FFAR4 cDNA (NM_181745) is placed downstream of an appropriate promoter sequence;

b introducing the chimeric gene into an adipose stem cell or an adipose precursor cell by incorporating the chimeric gene into a virus or the like; and c differentiating the adipose stem cell or the adipose precursor cell in which the chimeric gene has been introduced to adipocytes.

(9) The method according to item 8, in which the promoter sequence is an aP2 gene promoter sequence.

(10) A transplant composition including the adipocytes according to item 1, for treating and/or preventing a disease.

(11) The transplant composition according to item 10, in which the disease is a decrease in glucose tolerance associated with aging.

(12) The transplant composition according to item 10, in which the disease is a decrease in cognitive ability associated with aging.

(13) A method for treating and/or preventing a disease, including: transplanting the transplant composition according to item 10 into a human.

(14) The method according to item 13, in which the transplant composition contains adipocytes obtained by forcibly expressing FFAR4 in an adipose stem cell or an adipose precursor cell collected from the human through gene introduction, and then inducing differentiation thereto to obtain adipocytes.

(15) A method for treating and/or preventing a disease, including: transplanting the transplant composition according to item 10 into an animal (excluding a human).

(16) The method according to item 15, in which the transplant composition contains adipocytes obtained by forcibly expressing FFAR4 in an adipose stem cell or an adipose precursor cell collected from the animal through gene introduction, and then inducing differentiation thereto to obtain adipocytes.

(17) A transgenic mouse including an adipose tissue in which a gene encoding FFAR4 has been introduced to forcibly express FFAR4.

(18) The transgenic mouse according to item 17, in which the transgenic mouse is produced by a method including:

a creating a chimeric gene in which human FFAR4 cDNA (NM_181745) is placed downstream of an appropriate promoter sequence; and b introducing the chimeric gene into a fertilized mouse egg.

(19) The transgenic mouse according to item 18, in which the promoter sequence in the step a is a mouse aP2 gene promoter sequence.

DESCRIPTION OF THE INVENTION

Figure 1:
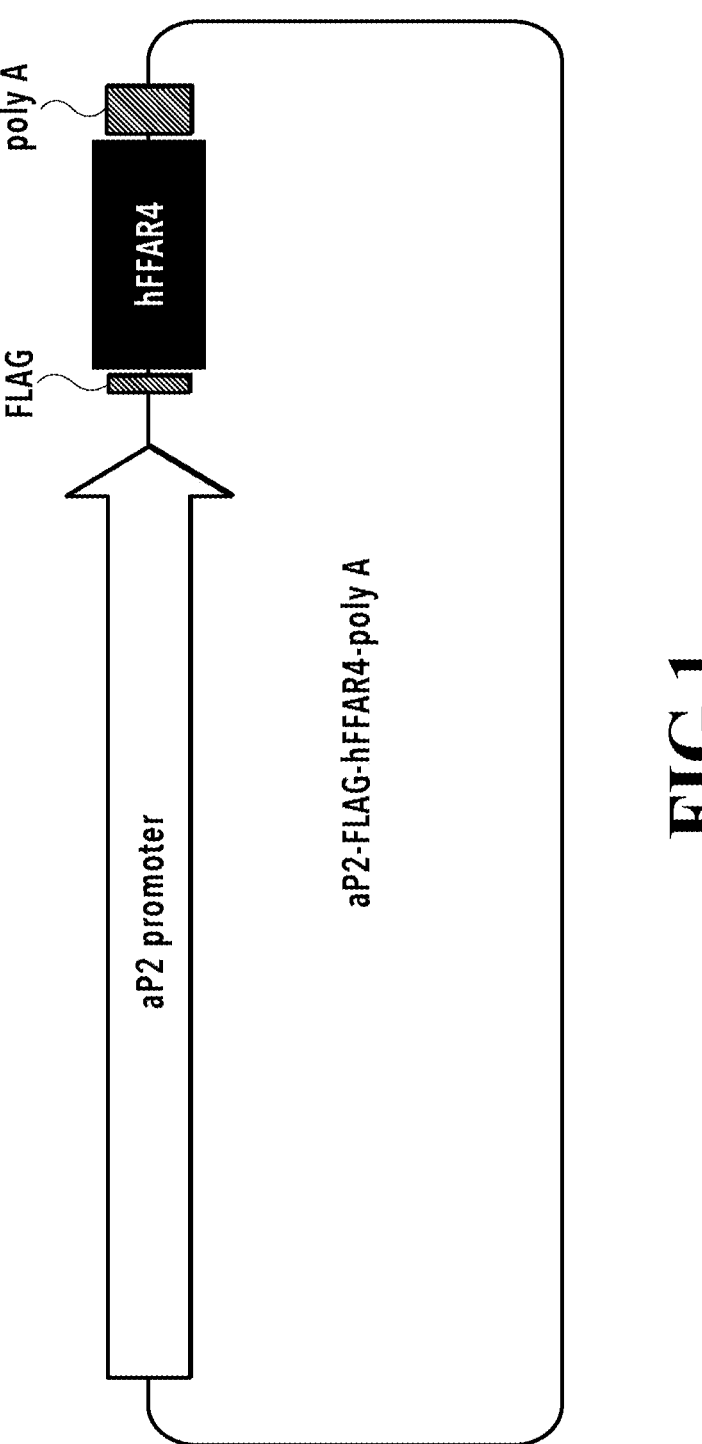
FIG. 1 shows a plasmid used in constructing a transgenic mouse in which FFAR4 is overexpressed in an adipose tissue. The expression of the human FFAR4 gene is controlled by a protein aP2 promoter which is expressed in adipose tissues. For this reason, the expression of the human FFAR4 is limited to adipose tissues.

The present invention provides adipocytes over-expressing FFAR4 useful in treating and/or preventing various diseases, and a method for treating and/or preventing various diseases using the cells. The adipocytes over-expressing FFAR4 in the present invention are adipocytes which are modified by introducing a gene encoding FFAR4 in the adipocytes to express FFAR4, and include, for example, adipose stem cells or adipose precursor cells derived from adipose tissues, which are forced to express FFAR4 by introducing a FFAR4 gene into the adipose stem cells or adipose precursor cells, and then inducing differentiation thereto, and those isolated from adipose tissues of transgenic mice in which a gene encoding FFAR4 has been introduced.

An embodiment of the present invention will be specifically described below; however, the following description is for facilitating the understanding of the present invention, and the scope of the present invention is not limited to the following embodiment, and the scope of the present invention also encompasses other embodiments obtained by a person skilled in the art substituting the configuration of the following embodiment as appropriate.

1. Description of Terms

The terms frequently used in the Specification will be defined, and the configurations thereof will be specifically described. Note that the definitions described below in this section are commonly used in the other aspects of the present invention unless otherwise noted.

In the Specification, the "adipose tissue" is one of connective tissues creating a body of a living organism, and is present mainly under the skin. The adipose tissue mainly contains mature adipocytes, and has functions of storing energy, protecting the body against physical impacts and changes in temperature from the outside, and secreting hormones, cytokine, and the like. In the Specification, the "adipose tissue" is sometimes described as "adipose".

In the Specification, the "stem cell" means a cell having differentiation potential to various cells and a potential for self-renewal.

In the Specification, the "adipose stem cell" refers to a somatic stem cell that is derived from adipose tissues and satisfies definitions (1) to (4) described below.

Definitions of Adipose Stem Cell (1) is derived from adipose tissues
(2) exhibits adhesiveness to a plastic under culture conditions in a standard medium
(3) exhibits positive for CD90, CD73, and CD105 in flow cytometry
(4) exhibit negative for CD31 and CD45 in flow cytometry The adipose stem cells in the present invention have at least differentiation potential to adipocytes.

In the present invention, "adipose precursor cells" capable of differentiating to adipocytes can be used instead of "adipose stem cells".

The "FFAR4" in the present invention is one of G protein-coupled receptors and is confirmed to be expressed in the large intestines, the adipose tissues, the lungs, and the like. The amino acid sequence of "FFAR4" is registered as NP_859529 in the GenBank.

2. Adipocytes Modified to Express FFAR4

The "adipocytes over-expressing FFAR4" in the present invention mean adipocytes that are modified to express FFAR4 from artificially introduced genes and constantly over-express FFAR4 more than normal adipocytes that are not subjected to gene introduction. The degree of over-expression is, for example, 1.3 to 50000 times, and particularly 1.3 to 100 times the standard number of expression.

The adipocytes over-expressing FFAR4 in the present invention can be produced by introducing the FFAR4 gene into an adipose stem cell or an adipose precursor cell derived from adipose tissue, and then inducing differentiation thereto.

For example, the adipocytes over-expressing FFAR4 can be produced by a method comprising:

a creating a chimeric gene in which the human FFAR4 cDNA (NM_181745) was placed downstream of an appropriate promoter sequence;

b introducing the chimeric gene into an adipose stem cell or an adipose precursor cell by incorporating the chimeric gene into a virus or the like; and c differentiating the adipose stem cell or the adipose precursor cell in which the chimeric gene has been introduced to adipocytes.

Here, the term "promoter" is defined as a DNA sequence recognized by the synthetic machinery of the cell, or introduced synthetic machinery, required to initiate a specific gene transcription, and refers to a nucleic acid fragment that functions to control the transcription of one or more polynucleotides, located upstream of a polynucleotide sequence (s), and that is structurally identified by the presence of a binding site for DNA-dependent RNA polymerase, transcription initiation sites, and any other DNA sequences including, but not limited to, transcription factor binding sites, repressor, and activator protein binding sites, and any other sequences of nucleotides known in the art to act directly or indirectly to regulate the amount of transcription from the promoter.

As the "appropriate promoter sequence", any promoter sequence can be used as long as the above gene can be operably linked to the promoter sequence. In addition, "operably linked" is defined such that the promoter is present at a correct position and direction relative to a nucleic acid to control the initiation of the RNA polymerase and the expression of the gene.

In addition, as the "promoter", a specific promoter used to control expression of a polynucleotide sequence of interest is not considered to be important as long as the specific promoter is capable of directing the expression of the polynucleotide in a targeted cell. Thus, in the case where a human cell is targeted, the polynucleotide sequence coding region may, for example, be placed adjacent to and under the control of a promoter that is capable of being expressed in a human cell. Generally speaking, such a promoter might include either a human promoter or a viral promoter.

In various embodiments, a human cytomegalovirus (CMV) immediate early gene promoter, an SV40 early promoter, a Rous sarcoma virus long terminal repeat, (3-actin, a rat insulin promoter, and a glyceraldehyde-3-phosphate dehydrogenase can be used to achieve high level expression of a target coding sequence. As long as the expression level is sufficient in a given object, any other viral promoter, or mammalian cellular promoter, or bacterial phage promoter which are known in the field to achieve expression of a target coding sequence can also be similarly used. The level and pattern of expression of a target protein after transfection or after transformation can be optimized by using a promoter having well-known properties.

The above-described promoter sequence includes the aP2 gene promoter sequence.

As the method for introducing a chimeric gene into an adipose stem cell or adipose precursor cell, a gene introduction method using a viral vector or a non-viral vector can be used.

The "vector" refers to a construct capable of being introduced into a host cell and expressing optionally one or more target polynucleotides in the Specification. Examples of the vector include, but are not limited to, viral vectors, naked DNA or RNA expression vectors, plasmids, cosmids or phage vectors, DNA or RNA expression vectors associated with cationic condensing agents, DNA or RNA expression vectors encapsulated in liposomes, and certain eukaryotic cells such as producer cells. The vector can be stable and can be self-replicating. The type of the vector that can be used is not particularly limited. The vector can be a cloning vector, suitable for propagation and for obtaining polynucleotides, gene constructs, or expression vectors incorporated to several heterologous organisms. Suitable vectors include prokaryotic expression vectors (for example, pUC18, pUC19, Bluescript, and their derivatives), mp18, mp19, pBR322, pMB9, CoIE1, pCR1, RP4, phages, and shuttle vectors (for example, pSA3 and pAT28), and eukaryotic expression vectors based on viral vectors (for example, adenoviruses, adeno-associated viruses as well as retroviruses and lentiviruses), as well as non-viral vectors, for example, pSilencer 4.1-CMV (Ambion (registered trademark), Life Technologies Corp., Carslbad, CA, US), pcDNA3, pcDNA3.1/hyg pH CMV/Zeo, pCR3.1, pEFl/His, pIND/GS, pRc/HCMV2, pSV40/Zeo2, pTRACER-HCMV, pUB6/V5-His, pVAX1, pZeoSV2, pCI, pSVL, and pKSV-10, pBPV-1, pML2d, and pTDT1.

In addition, the method for producing adipocytes expressing FFAR4 from an artificially introduced gene includes, for example, a method that includes forcibly expressing FFAR4 in an adipose stem cell or an adipose precursor cell collected from a human or an animal through gene introduction, and then differentiating the adipose stem cell or the adipose precursor cell to adipocytes, and a method that includes constructing transgenic mice in which a gene encoding FFAR4 was introduced to obtain adipocytes.

The degree of expression of FFAR4 can be measured, for example, by an immunological method using an anti-FFAR4 antibody (western blotting or the like), or a method for quantitatively analyzing the mRNA (RT-PCR or the like).

The adipocytes modified to express FFAR4 by the present invention are used to treat and/or prevent various diseases, particularly a decrease in glucose tolerance associated with aging, a decrease in cognitive ability associated with aging.

3. Transgenic Mouse

A transgenic mouse into which the gene encoding FFAR4 is introduced can be constructed by a method comprising:

a creating a chimeric gene in which the human FFAR4 cDNA (NM_181745) is placed downstream of an appropriate promoter sequence; and b introducing the chimeric gene into fertilized mouse eggs.

As the above-described promoter sequence, the same as those described above are used, including, for example, the aP2 gene promoter sequence.

In addition, as the method for introducing the chimeric gene into fertilized eggs, the same method as the above-described method for introducing the chimeric gene into adipose stem cells or adipose precursor cells is used.

In the method of the present invention, diseases to be treated or prevented are typically, but are not limited to, a decrease in glucose tolerance and a decrease in cognitive ability associated with aging.

In addition, in the Specification, the "treatment" means improving the symptom of a disease of a patient or test subject or delaying the progress of the symptom, and the "prevention" means preventing the onset of a disease of a patient or test subject in advance. The "patient or test subject" is typically a human, but may be an animal other than a human. The animal other than a human includes, but is not limited to, for example, mammals such as a dog, a cat, cattle, a horse, a pig, a goat, sheep, a monkey (a crab-eating monkey, a rhesus macaque, a common marmoset, a Japanese macaque), a ferret, a rabbit, rodents (a mouse, a rat, a Mongolian gerbil, a guinea pig, a hamster), and birds such as a chicken and a quail.

4. Transplant Composition

A transplant composition comprising the adipocytes over-expressing FFAR4 is adjusted to a cell concentration of, for example, $0.2 \times 10^7$ to $2 \times 10^7$/ml in an appropriate medium, and is injected into subcutaneous tissues or adipose tissues, preferably subcutaneous tissues of a human or an animal as it is or after further mixed with an effective medium, preferably, a solution containing an extracellular matrix such as collagen, or the like.

The usable medium is not particularly limited as long as the medium is any pharmaceutically acceptable medium, that is, a liquid that can be administered to a patient or test subject. The pharmaceutically acceptable medium includes, but is not limited to, for example, water for injection, physiological saline solution, media, 5% glucose solution, hyaluronic acid solution, Ringer's solution, lactated Ringer's solution, acetated Ringer's solution, bicarbonated Ringer's solution, BICANATE (registered trademark) transfusion, amino acid solution, initiation solution (solution I), rehydration solution (solution II), maintenance transfusion (solution III), postoperative recovery solution (solution IV), Plasma-Lyte A (registered trademark), and the like.

The transplant composition of the present invention may comprise additives that can be administered to a patient or test subject and can adjust preservation stability, isotonicity, absorbance, and/or viscosity, and the like of the transplant composition. The above additives include, but are not limited to, for example, an emulsifier, a dispersant, a buffer, a preservative, a humectant, an antioxidant, a chelating agent, a thickener, a gellant, a pH adjuster, and the like. The thickener includes, but is not limited to, for example, HES, dextran, methyl cellulose, xanthan gum, carboxymethyl cellulose, hydroxypropyl cellulose, and the like. The concentration of the additives may be set as desired as long as the additives are safe in the case of administration to a patient or test subject.

The transplant composition of the present invention may comprise any component that can be administered to a patient or test subject. The above-described component includes, but is not limited to, for example, salts, polysaccharides (for example, hydroxyethyl starch (HES), dextran, and the like), proteins (for example, albumin and the like), dimethyl sulfoxide (DMSO), amino acids, medium components, and the like.

The pH of the transplant composition of the present invention may be, but is not limited to, a pH near neutral, for example, a pH of 5.5 or more, a pH of 6.0 or more, a pH of 6.5 or more, or a pH of 7.0 or more, and may be a pH of 10.5 or less, a pH of 9.5 or less, a pH of 8.5 or less, or a pH of 8.0 or less.

The cell concentration of the transplant composition of the present invention may be any cell concentration that allows the composition to be administered to a patient or test subject, although it varies depending on the administration method as well as the age, the body weight, and the symptom of the patient or test subject, and the like. The lower limit of the cell concentration is not particularly limited, but may be, for example, $1.0 \times 10^5$ cells/mL or more, $2.0 \times 10^5$ cells/mL or more, $4.0 \times 10^5$ cells/mL or more, $6.0 \times 10^5$ cells/mL or more, $8.0 \times 10^5$ cells/mL or more, $1.0 \times 10^6$ cells/mL or more, $2.0 \times 10^6$ cells/mL or more, $4.0 \times 10^6$ cells/mL or more, $6.0 \times 10^6$ cells/mL or more, $8.0 \times 10^6$ cells/mL or more, or $1.0 \times 10^7$ cells/mL or more. The upper limit of the cell concentration is not particularly limited, but may be, for example, $1.0 \times 10^{10}$ cells/mL or less, $1.0 \times 10^9$ cells/mL or less, $8.0 \times 10^8$ cells/mL or less, $6.0 \times 10^8$ cells/mL or less, $4.0 \times 10^8$ cells/mL or less, $2.0 \times 10^8$ cells/mL or less, or $1.0 \times 10^8$ cells/mL or less.

The dose of the adipocytes over-expressing FFAR4 is around $10^2$ to $10^{10}$ cells/individual, and is around $2 \times 10^5$ to $2 \times 10^8$ cells/individual in the case of administration to a human.

The frequency of administration of the transplant composition of the present invention is a frequency that allows a patient or test subject to obtain therapeutic effects on the disease in the case where the composition is administered to the patient or test subject. A specific frequency of administration can be determined as appropriate depending on the mode of administration, the administration method, as well as the age, the body weight, and the symptom of the patient or test subject, and the like, and is, for example, once every 5 years, once per year, once every 6 months, once every 3 months, once every 8 weeks, once every 6 weeks, once every 4 weeks, once every 3 weeks, once every 2 weeks, once per week, twice per week, three times per week, four times per week, five times per week, six times per week, or seven times per week, and particularly preferably once per year, once every 6 months, once every 3 months, once every 8 weeks, once every 6 weeks, or once every 4 weeks.

The administration period of the transplant composition of the present invention is a period that allows a patient or test subject to obtain treatment or prevention effects in the case where to whom the composition administered to the patient or test subject. Specific administration period can be determined as appropriate depending on the mode of administration, the administration method, as well as the age, the body weight, and the symptom of the patient or test subject, and the like, but the transplant composition of the present invention can be administered for a long period of time, and can be administered, for example, on a 10-year basis, or on a several-year basis. However, since it is confirmed that the effects of the transplant composition of the present invention maintain at least around 6 to 8 weeks with one administration, treatment with a single administration is also possible, and multiple administrations are not necessarily needed.

EXAMPLES

The present invention will be described in further detail based on Examples given below; however the present invention is not limited to these Examples.

Example 1

Glucose Tolerance Test and Novel Object Recognition Test in FFAR4-TG Mouse

1. Construction of FFAR4-TG Mice

The work was assigned to Transgenic Inc. A chimeric gene in which the human FFAR4 cDNA (NM_181745) having a FLAG-tag sequence at the N terminal was placed downstream of a mouse aP2 gene promoter sequence was created. Moreover, the polyadenylation signal was placed downstream of the human FFAR4 cDNA. As reported before, the human FFAR4 cDNA was obtained by the PCR method (1). This chimeric gene was administered to C57BL/6 fertilized mouse eggs by the microinjection method. The mice thus obtained were fed a normal diet ad libitum, and bred under a 12-hour light-dark cycle.

FIG. 1 shows a plasmid used to construct the FFAR4-TG mice. The expression of the human FFAR4 gene is controlled by a protein aP2 promoter which is expressed in adipose tissues. For this reason, the expression of the human FFAR4 is limited to adipose tissues.

Figure 2:
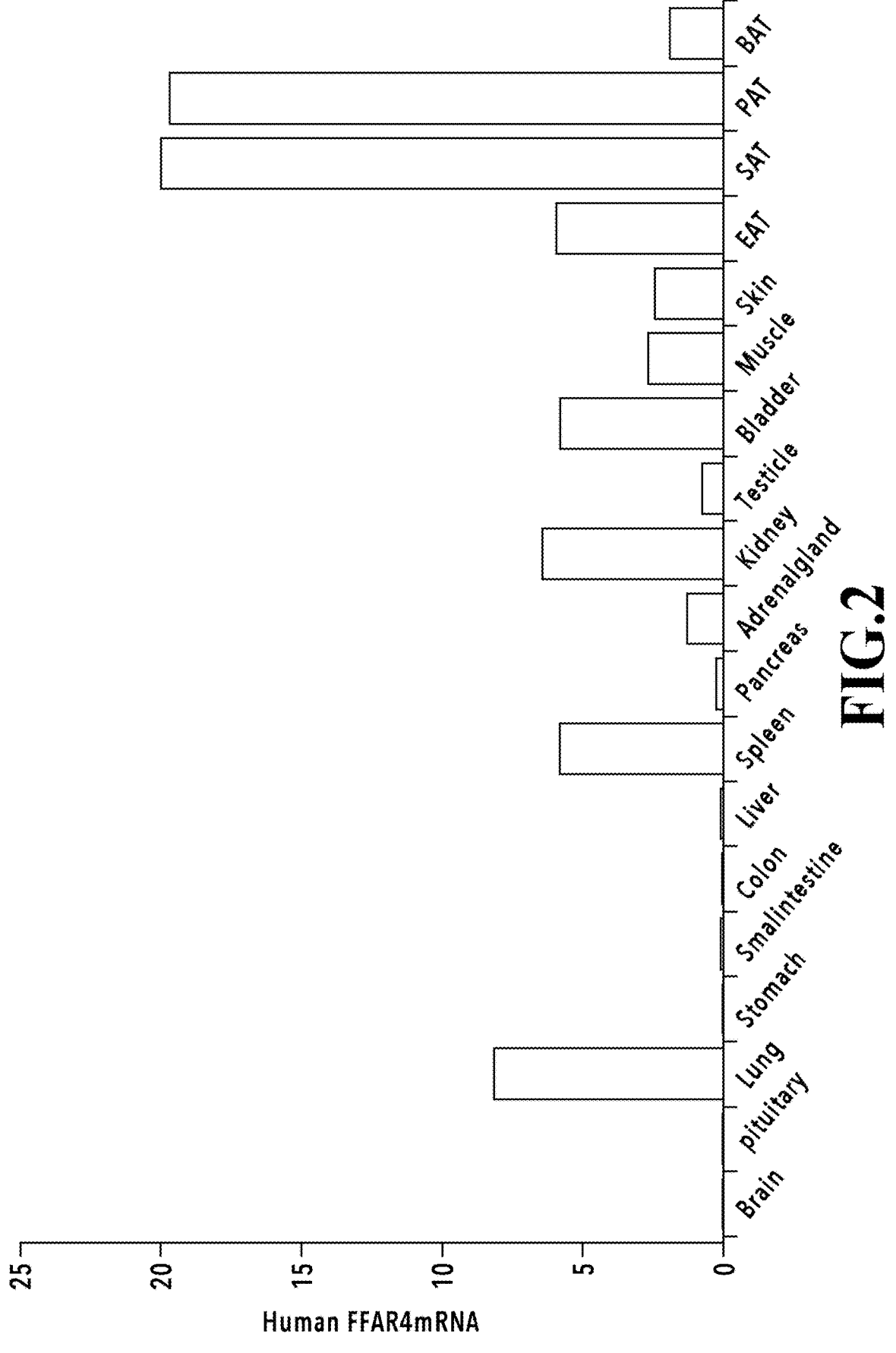
FIG. 2 shows a comparison of the expression of the human FFAR4 gene in each organ of the constructed transgenic (FFAR4-TG) mice by a RT-PCR method. While strong expression was observed in the white adipose tissues of the subcutaneous adipose (SAT) and the visceral adipose (PAT), the expression was weak in other organs such as the brown adipocytes (BAT).

The expression of the human FFAR4 gene in each organ of the constructed transgenic (FFAR4-TG) mice was compared by a RT-PCR method. While strong expression was observed in the white adipose tissues of the subcutaneous adipose (SAT) and the visceral adipose (PAT), the expression was weak in other organs such as the brown adipocytes (BAT). (FIG. 2)

2. Glucose Resistance Test Method

Scars were formed in tail portions of mice fasted for 24 hours by using a razor to obtain peripheral bloods, and the blood glucose concentrations were measured using One Touch Ultra (LifeScan Inc.) as fasting glucose concentrations. Thereafter, 1.5 mg of glucose per g of the body weight was administered to the abdominal cavities. The blood was collected after 15, 30, 60, 90, and 120 minutes, and the blood glucose concentrations were measured in the same way.

3. Novel Object Recognition Test Method

The novel object recognition test was conducted while the method described in the past paper was modified (2-4). The mice were allowed to freely explore an open field for 5 minutes over 3 days. In day 4, two identical substances were placed in the open field, and the mice were allowed to freely explore for 10 minutes. Each mouse was returned to the cage where the mouse was bred, and given free for 6 hours. Then, one of the two substances was substituted with a novel object that the mice did not know, and the mice was again allowed to explore for 10 minutes. The time for which the mice explored each substance was measured.

Figure 9:
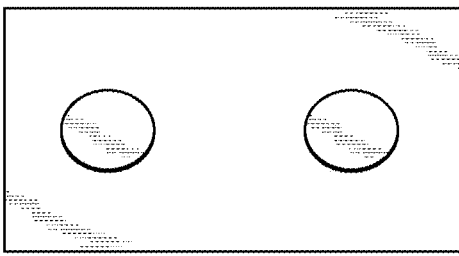
FIG. 9 is a diagram showing a general presentation of a novel object recognition test. Mice are first allowed to freely explore, and to learn placed substances (shown by circles in the drawing) (upper stage). (the learned substances serve as "familiar objects") After the elapse of 6 hours, one of the familiar objects is replaced with a novel object (shown by a rhombus in the drawing), and the mice are again allowed to explore. The total exploration time and the exploration time to the novel object at this time are measured.
Figure 9:
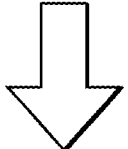
Figure 9:
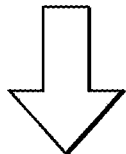
Figure 9:
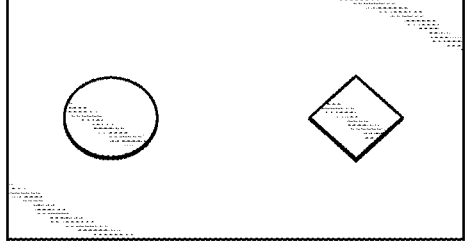
Figure 10:
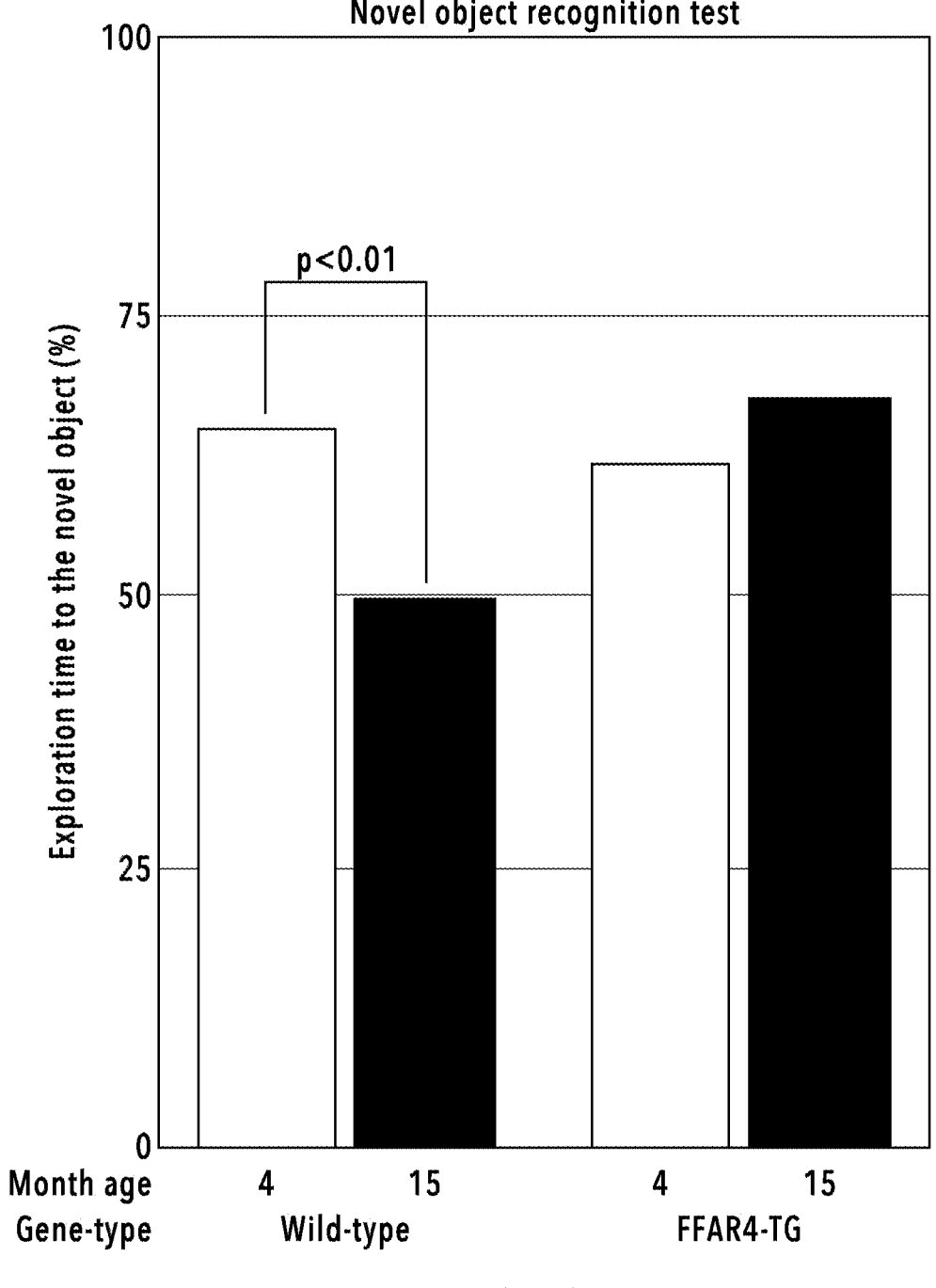
FIG. 10 shows results of the novel object recognition test in wild-type mice and FFAR4-TG mice.

Specifically, the mice are first allowed to freely explore to learn the familiar objects (the upper part of FIG. 9). After 6 hours, one of the familiar objects is replaced with the novel object, and the mice are again allowed to explore (the lower part of FIG. 9). The total exploration time and the exploration time to the novel object at this time are measured. (FIG. 10)

The cognition and the memory of the wild-type mice and the FFAR4-TG mice to the novel object were measured in accordance with the novel object recognition test.

REFERENCES

Hirasawa, A. et al. Free fatty acids regulate gut incretin glucagon-like peptide-1 secretion through GPR120. Nat Med Jan; 11(1) 90-94 (2005)

Akkerman, S. et al. Object recognition testing: methodological considerations on exploration and discrimination measures. Behav Brain Res 232, 335-347 (2012).

Antunes, M. & Biala, G. The novel object recognition memory: neurobiology, test procedure, and its modifications. Cogn Process 13, 93-110 (2012).

Leger, M. et al. Object recognition test in mice. Nat Protoc 8, 2531-2537 (2013).

[Results]
1. Increases in Body Weight of FFAR4-TG Mice

Figure 3:
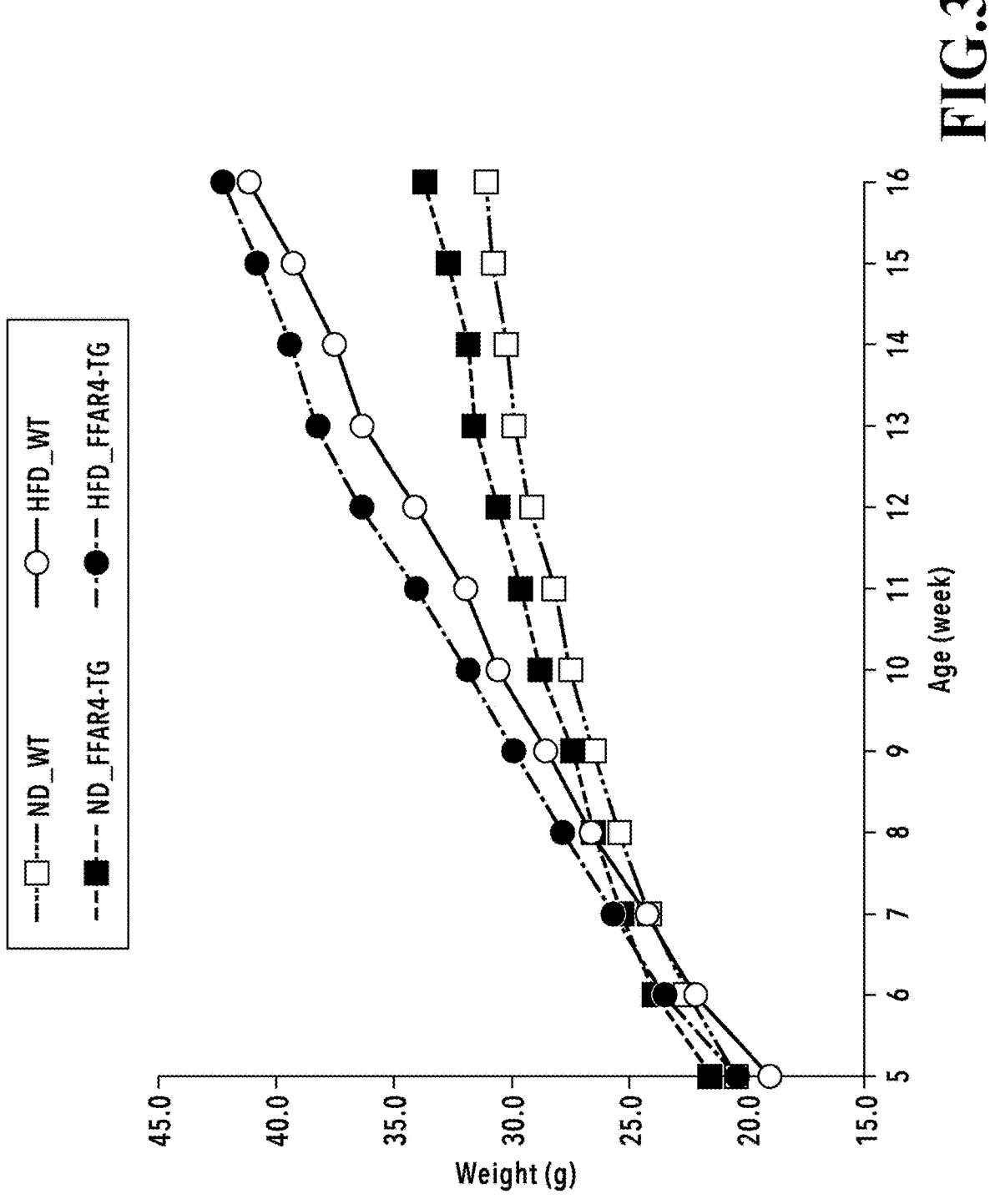
FIG. 3 is a graph showing results of comparing increases in body weight of the FFAR4-TG mice with those of normal mice. No significant change in body weight was found in either high-fat diet (HFD) or normal diet (ND).

Increases in body weight of the FFAR4-TG mice were compared with those of the normal mice. No significant change in body weight was found in either high-fat diet (HFD) or normal diet (ND). (FIG. 3)

2. Food Intake of FFAR4-TG Mice

Figure 4:
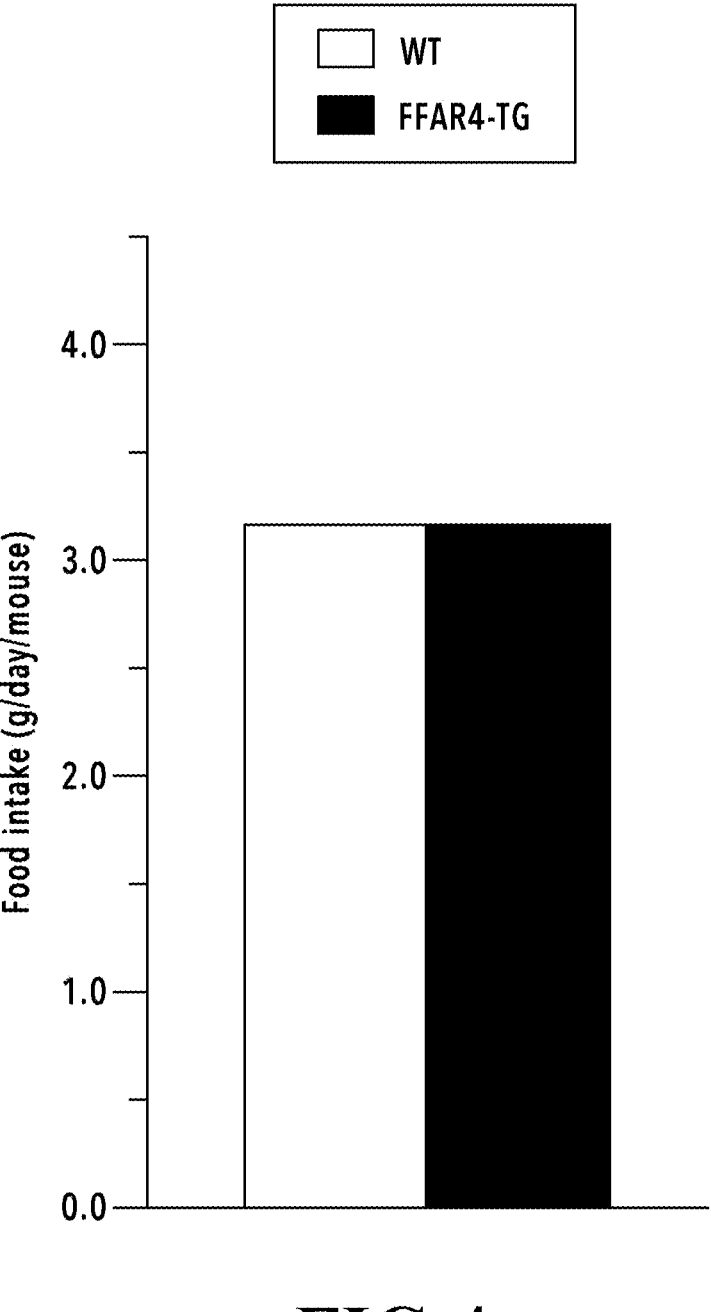
FIG. 4 is a graph showing results of comparing daily food intakes of FFAR4-TG mice with those of normal mice.

The daily food intakes of the FFAR4-TG mice were compared with those of the normal mice. No difference was found between them. (FIG. 4)

3. Glucose Tolerance of FFAR4-TG Mice

Figure 5:
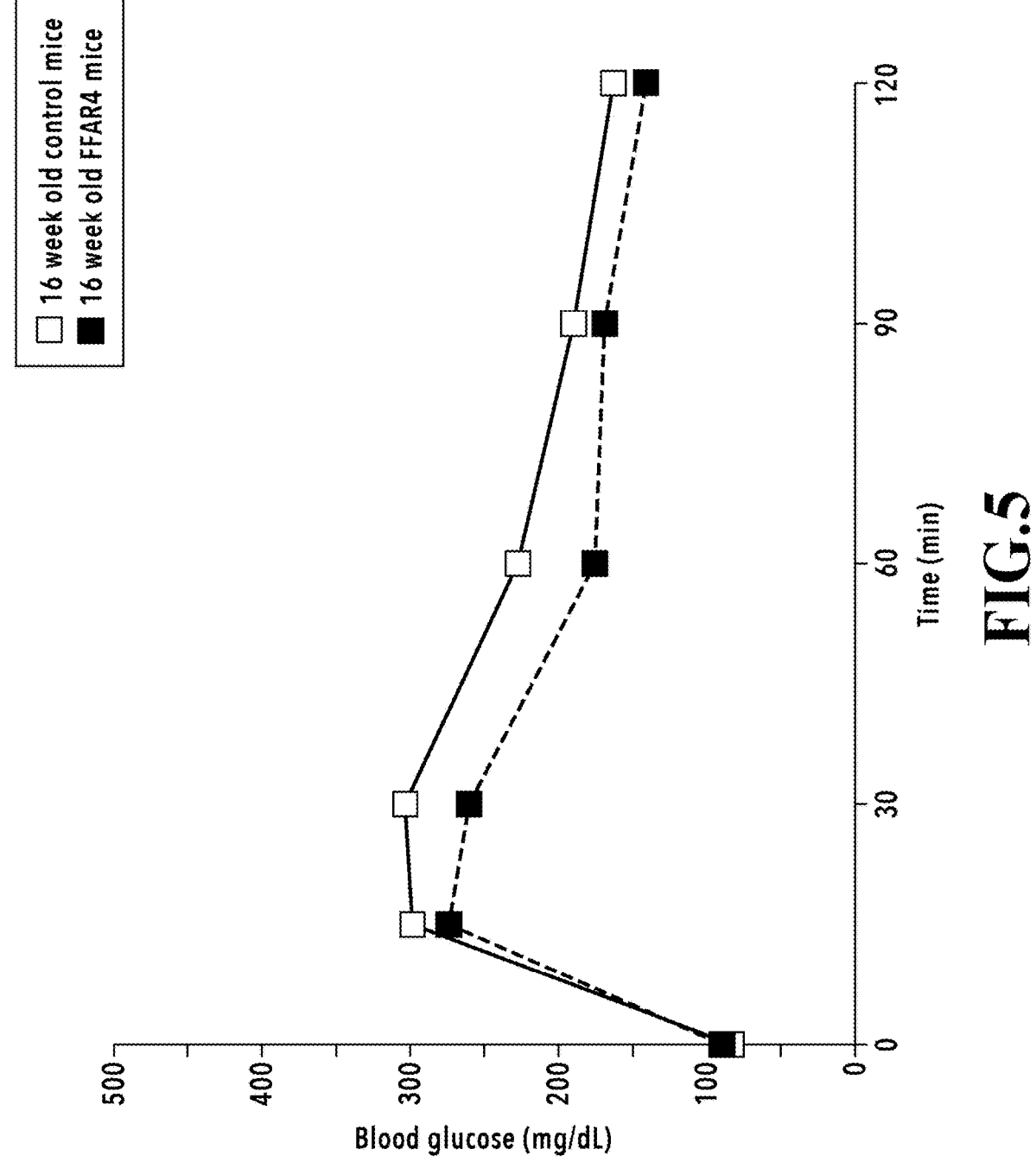
FIG. 5 is a graph showing results of comparing glucose tolerances of 16-week-old (4-month-old) FFAR4-TG mice with those of 16-week-old wild-type mice.

The glucose tolerances of 16-week-old (4-month-old) FFAR4-TG mice were compared with those of 16-week-old wild-type mice. No significant difference was found between them. (FIG. 5)

The glucose tolerance of 60-week-old (15-month-old) FFAR4-TG mice were compared with those of 60-week-old wild-type mice. In the wild-type mice, the glucose tolerances deteriorated due to aging, and in the 60-week-old

Figure 6:
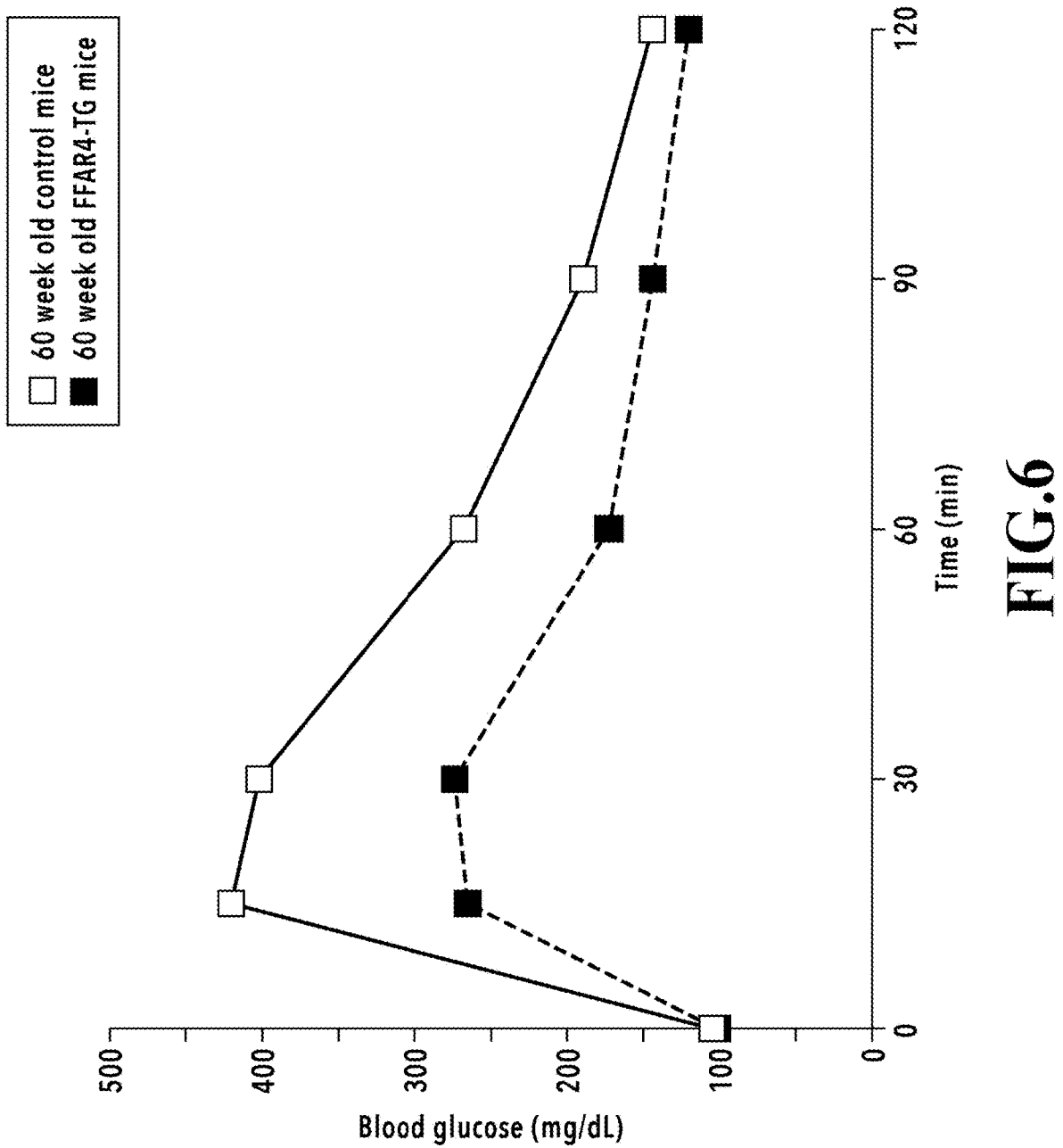
FIG. 6 is a graph showing results of comparing glucose tolerances of 60-week-old (15-month-old) FFAR4-TG mice with those of 60-week-old wild-type mice. In the wild-type mice, the glucose tolerances deteriorated due to aging, and in the 60-week-old wild-type mice, the blood sugar level was more significantly increased and decreased more slowly than in the 16-week-old wild-type mice. The 60-week-old FFAR4-TG mice exhibited substantially the same glucose tolerances as in the 16-week-old wild-type mice, and no deterioration in glucose tolerance associated with aging was found.

13 wild-type mice, the blood sugar level was more significantly increased and decreased more slowly than in the 16-week-old wild-type mice. In contrast, the 60-week-old FFAR4-TG mice exhibited substantially the same glucose tolerances as in the 16-week-old wild-type mice, and no deterioration in glucose tolerance associated with aging was found. (FIG. 6)

4. Novel Object Recognition Test in FFAR4-TG Mice

The 4-month-old wild-type mice had a longer exploration time to the novel object than the exploration time to the familiar object, and spent about 70% of the time in exploring the novel object. This indicates that the 4-month-old wild-type mice remembered the familiar object also after 6 hours. On the other hand, the cognitive abilities of the 15-month-old wild-type mice deteriorated due to aging, and the 15-month-old wild-type mice did not remember the familiar object after 6 hours, so that the exploration times to both substances were substantially equal, and the exploration time to the novel object decreased to about 50%. In contrast, the FFAR4-TG mice still remembered the familiar object even at the age of 15 months, and the exploration time to the novel object did not deteriorate. This indicates that the cognitive abilities of the FFAR4-TG mice are maintained at old ages as well. (FIG. 10)

Example 2

Glucose Tolerance Test and Novel Object Recognition Test in Mice Transplanted with Adipocytes Over-Expressing FFAR4

1. Cell Transplantation

Subcutaneous adipose tissues were collected from wild-type C57BL/6 mice and FFAR4-TG mice at the age of 16 months, and connective tissues and lymph nodes in the tissues were removed. After the tissue was cut into thin pieces, the Accumax (Funakoshi Co., Ltd.) enzymatic treatment was conducted at 37° C. for 1 hour, and the cell dispersion liquid subjected to a 100 μm-diameter mesh was centrifuged to obtain a precipitate. The precipitate was washed with PBS three times, and suspended in a solution composed of 153 mM $NH_4Cl$, 10 mM $HNaHCO_3$, 0.1 mM EDTA, and left to stand at room temperature for 10 minutes. After further washed with PBS two times, the cells were cultured in a DMEM/F12 medium containing 10% fetal bovine serum, 2 mM I-L-Alanyl-L-glutamate (Nakarai, Japan), and 1% penicillin/streptomycin for 6 hours. The bonded cells were further cultured for 5 days. After the culturing was started, at day 6, the medium was replaced with a DMEM/F12 containing 2% fetal bovine serum, 2 mM I-L-Alanyl-L-glutamate (Nakarai, Japan), 0.5 mM IBMX, 5 μM dexamethasone, 10 μM insulin, 200 μM indomethacin, and 1% penicillin/streptomycin, followed by further culturing for 2 days. The cells were collected using accutase (Funakoshi Co., Ltd.), suspended in Matrigel, and subcutaneously injected to 15-month-old mice so as to be in an amount of $2\times10^6$ cells/mouse.

2. Glucose Tolerance Test in Mice Transplanted with Adipocytes Over-Expressing FFAR4

The stem cells were separated from the adipose tissues of 16-month-old FFAR4-TG mice and wild-type mice, and cultured. Differentiation-induction to adipocytes was conducted for 2 days. Thereafter, the cells were suspended in Matrigel, and $2\times10^6$ cells per mouse were subcutaneously transplanted to the 15-month-old wild-type mice. The glucose tolerances were measured 8 weeks after the transplantation.

The glucose tolerances of the mice transplanted with wild-type mouse cells were not different from wild-type mice of the same age which did not transplanted with cells. The glucose tolerances of wild-type mice transplanted with the cells of the FFAR4-TG mice were significantly improved as compared with those of the control mice. (FIG. 7)

Figure 7:
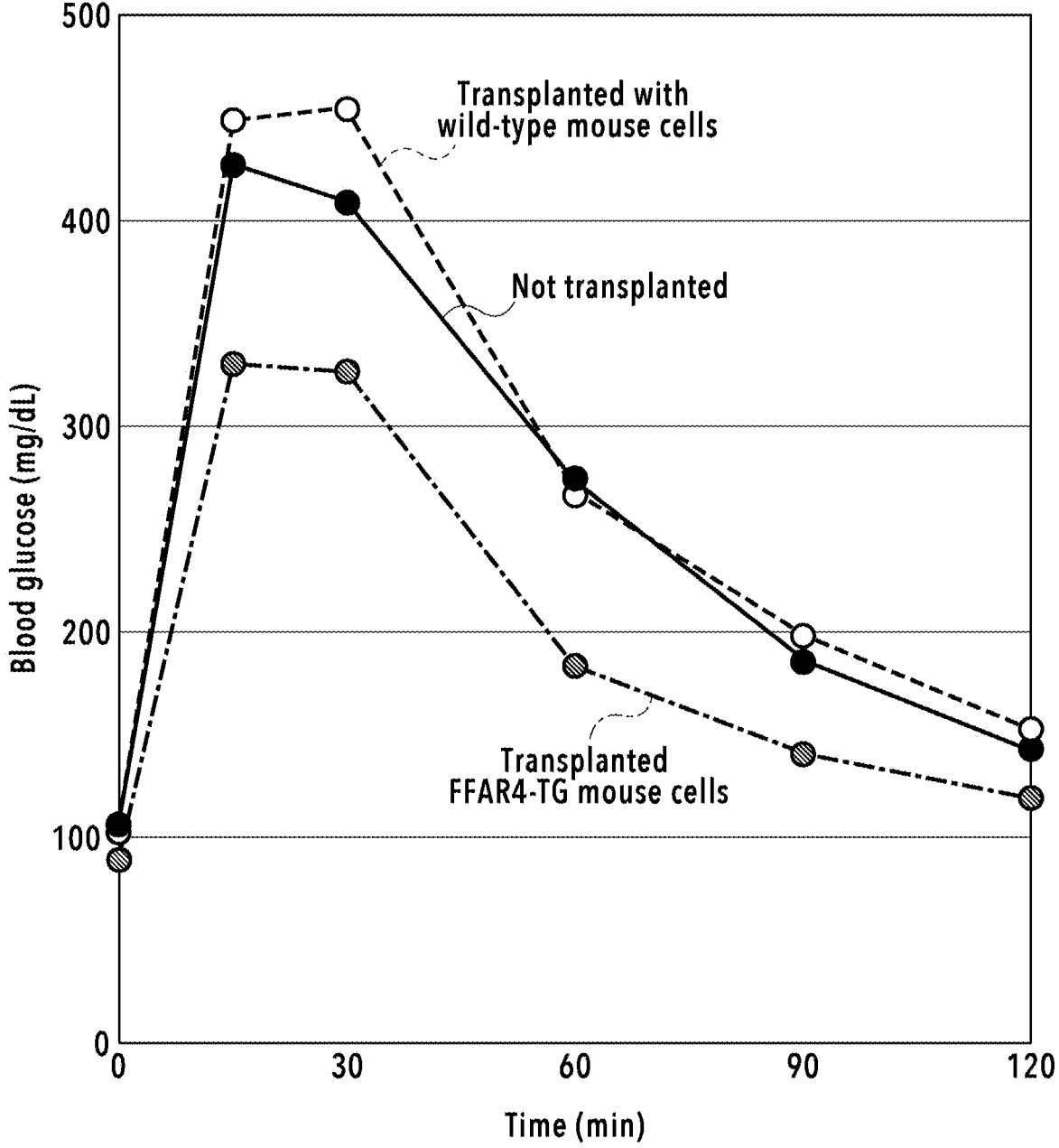
FIG. 7 is a graph in which glucose tolerances of wild-type mice transplanted with cells of the FFAR4-TG mice, mice transplanted with wild-type mouse cell, and wild-type mice which were not transplanted with cells were compared. The glucose tolerances of the wild-type mice transplanted with the cells of the FFAR4-TG mice were significantly improved as compared with those of the control mice.
Figure 8:
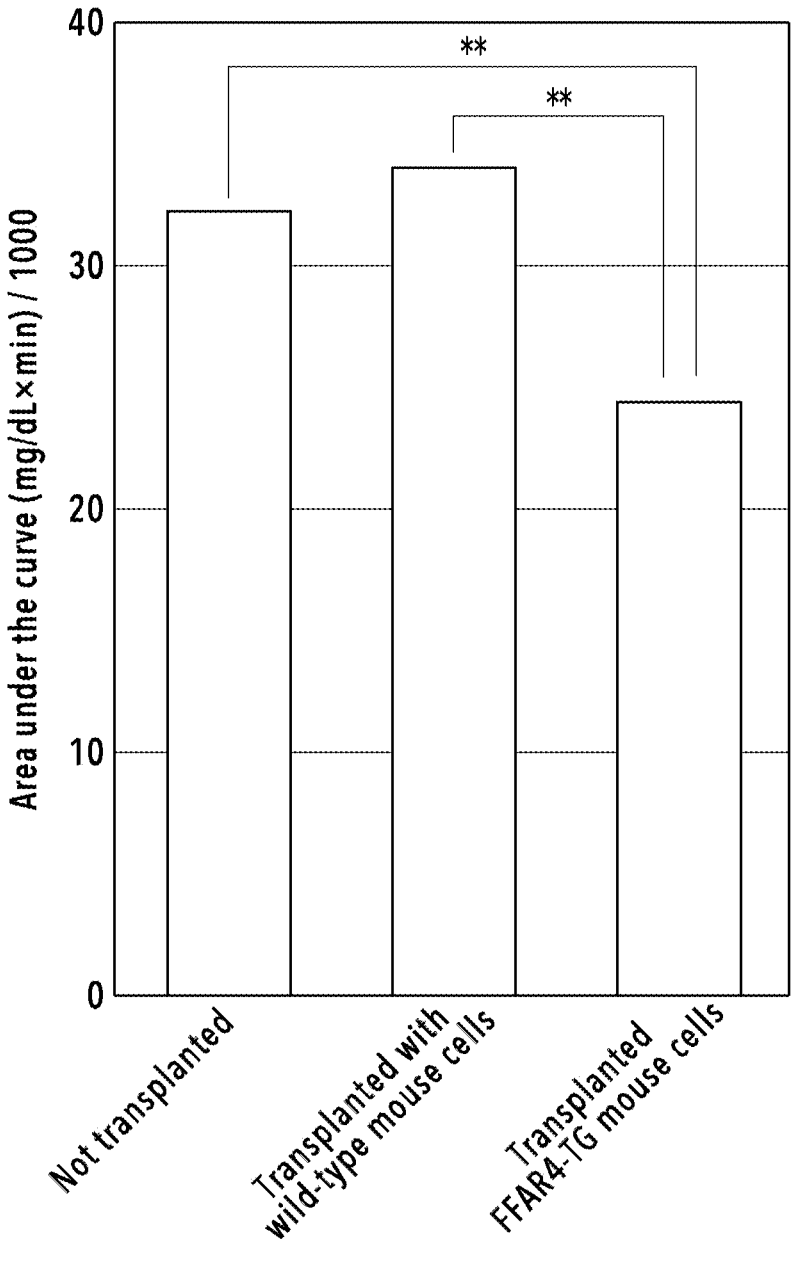
FIG. 8 is a graph formed from the area of a lower portion of the line graph of FIG. 7.

The bar graph of FIG. 8 is formed from the area under the curve (AUC) of the line graph of FIG. 7.

The results of FIG. 7 and FIG. 8 indicate that the transplantation of the adipocytes over-expressing FFAR4 can prevent or improve a decrease in glucose tolerance associated with aging.

3. Novel Object Recognition Test in Mice Transplanted with Adipocytes Over-Expressing FFAR4

The FFAR4-TG mouse-derived cells or the wild-type mouse-derived cells were transplanted into aged wild-type mice in the same method as in 3. of Example 1, and the novel object recognition test was conducted on the cell-transplanted mice.

Figure 11:
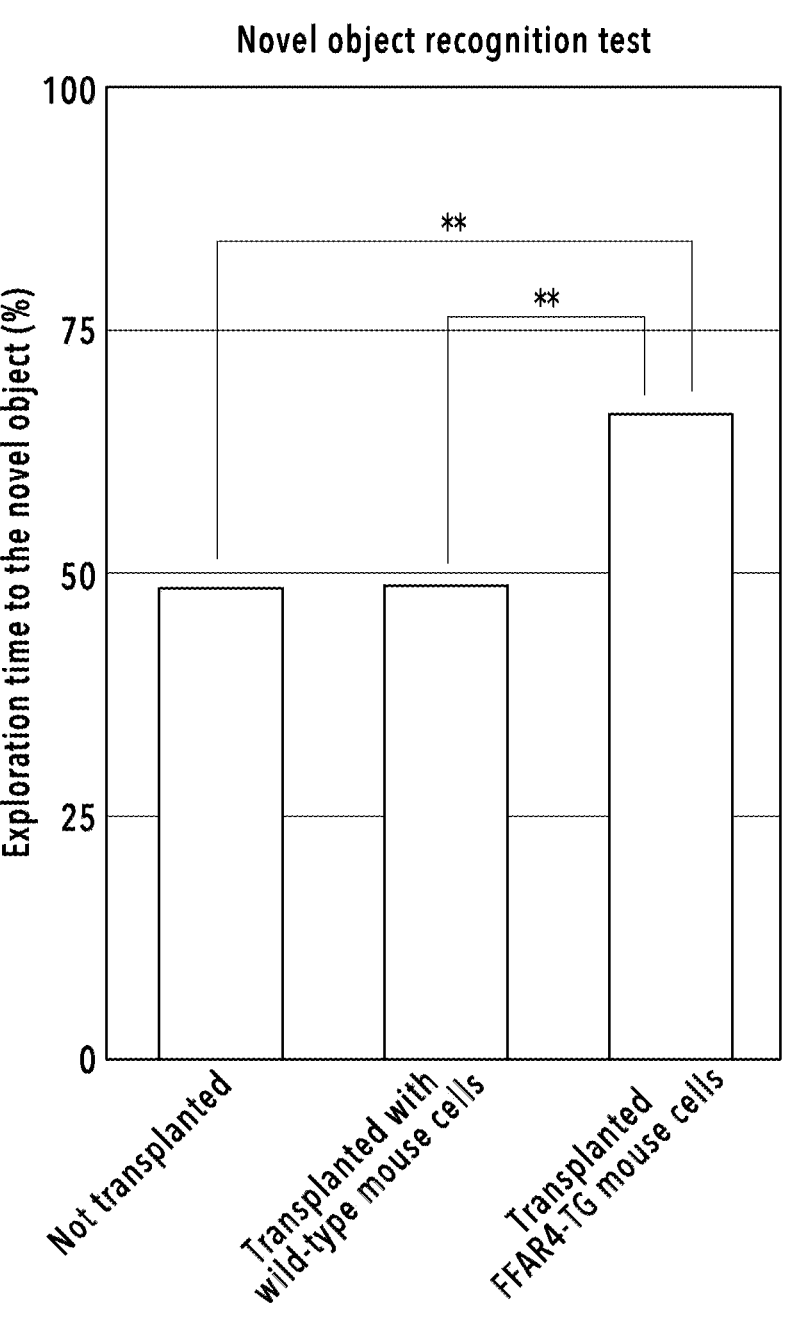
FIG. 11 shows results of the novel object recognition test in the wild-type mice transplanted with the cells of the FFAR4-TG mice, the mice transplanted with the wild-type mice cells, and the wild-type mice which were not transplanted with cells.

Even when the cells derived from the wild-type mice were transplanted into the aged wild-type mice, the exploration time to the novel object was around 50%, which was almost equal to those of the aged normal mice which were not subjected to the cell transplantation, and no improvement of cognitive ability was observed. However, when the FFAR4-TG mouse-derived cells were transplanted into the aged wild-type mice, a result indicating improvement of the cognitive ability was obtained (FIG. 11).

The above-described results indicate that the transplantation of the adipocytes over-expressing FFAR4 can prevent or improve a decrease in cognitive ability associated with aging.

Example 3

Glucose Tolerance Test and Novel Object Recognition Test in Adipose Stem Cell-Transplanted Mice Infected with FFAR4 Virus and Subjected to Differentiation-Induction An adeno-associated virus encoding the FFAR4 gene (FFAR4 virus) and its mock virus were purchased from Vector Builder Inc., and 16-month-old, male C57BL/6 mice were purchased from Charles River Laboratories.

The adipose tissue-derived stem cells obtained from the subcutaneous adiposes of the 16-month-old, male C57BL/6 mice were cultured for 5 days, and then infected with mock virus and FFAR4 virus. The medium was replaced with a differentiation-induction medium after 1 day, followed by culturing for 2 days. The cells were collected, and $1\times10^6$ cells were subcutaneously transplanted into newly prepared 16-month-old, male C57BL/6 mice. The novel object recognition test was conducted after 6 weeks, and the glucose tolerance test was conducted after 8 weeks.

Figure 12:
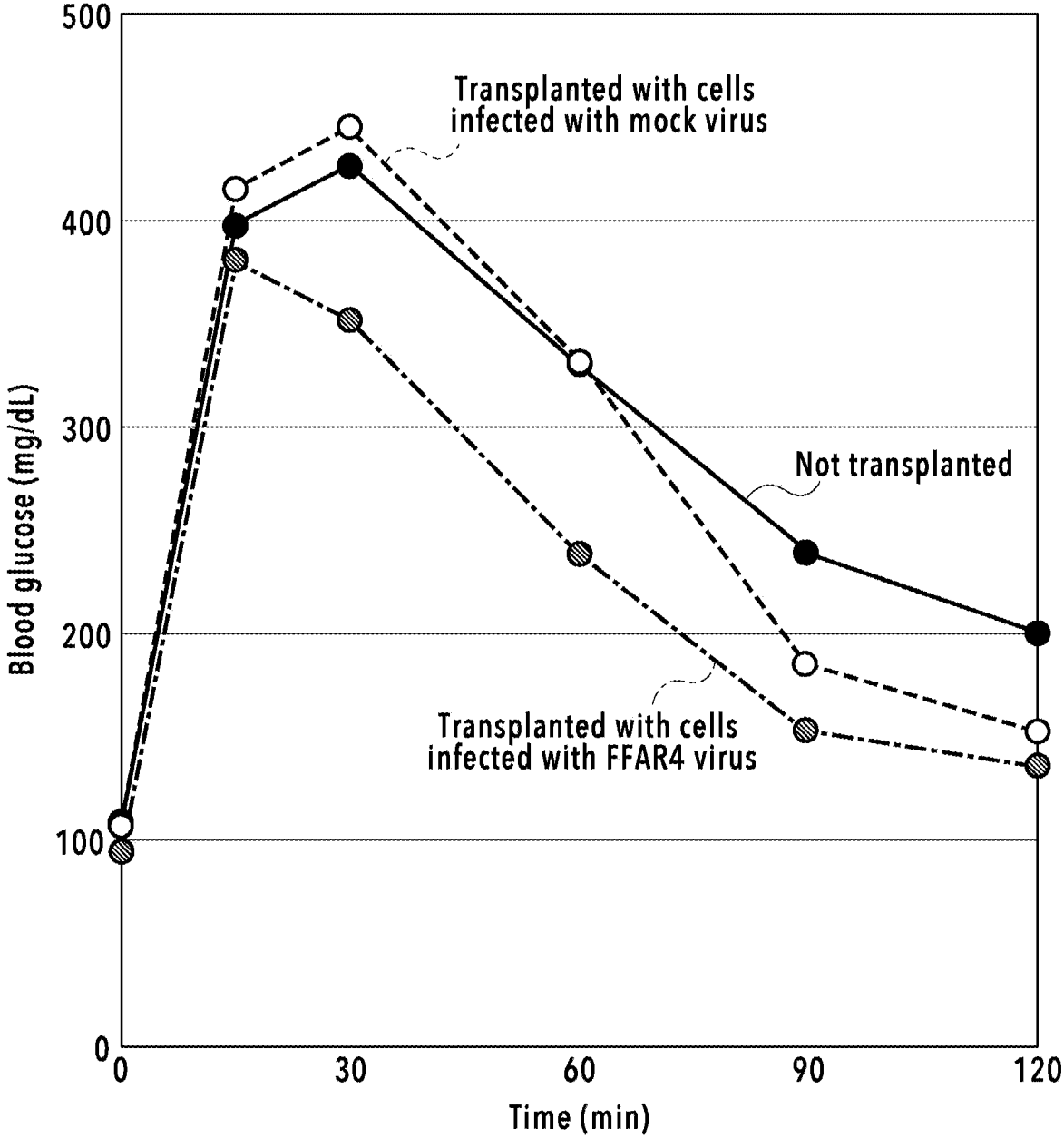
FIG. 12 shows results of a glucose tolerance test in mice subcutaneously transplanted with adipose stem cells which were infected with FFAR4 virus, and then inducing differentiation thereto.
Figure 13:
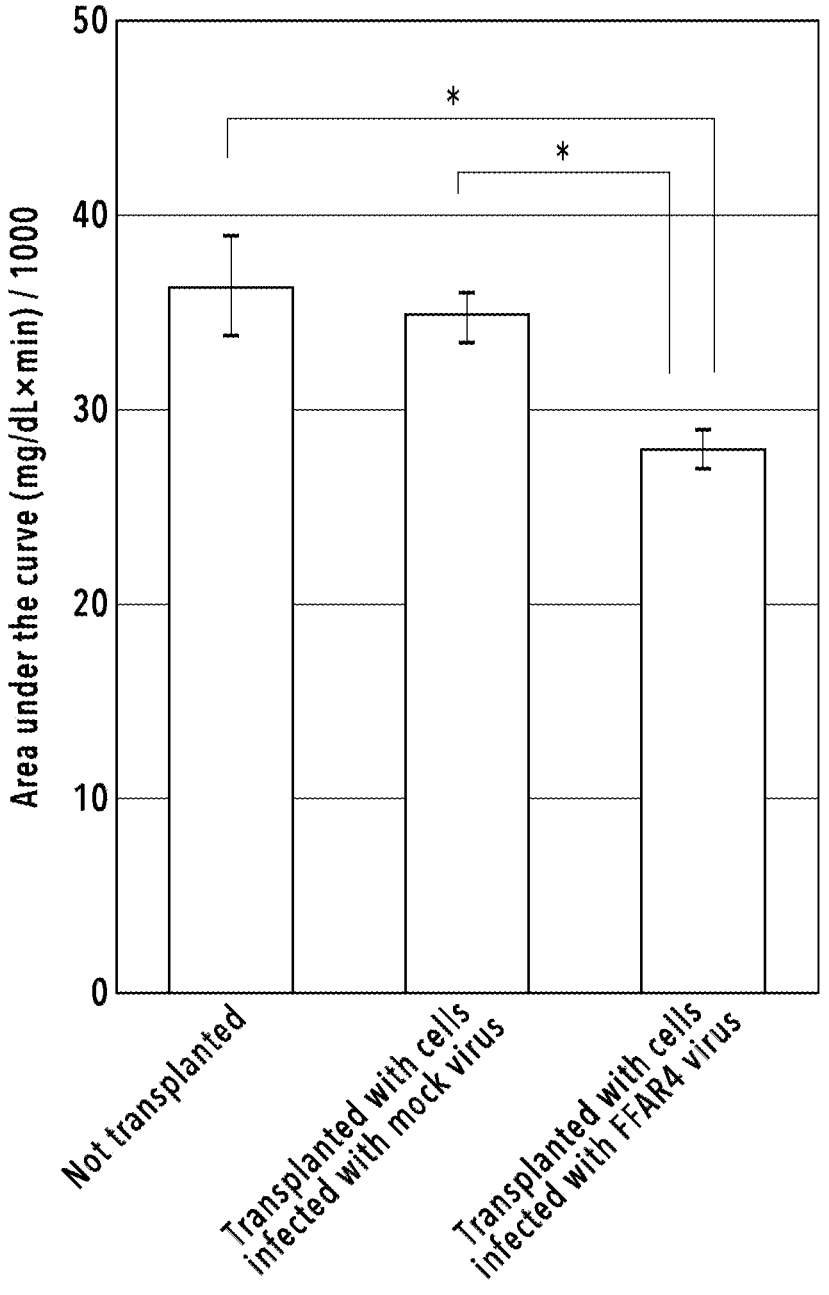
FIG. 13 is an area of the graph of FIG. 12.
Figure 14:
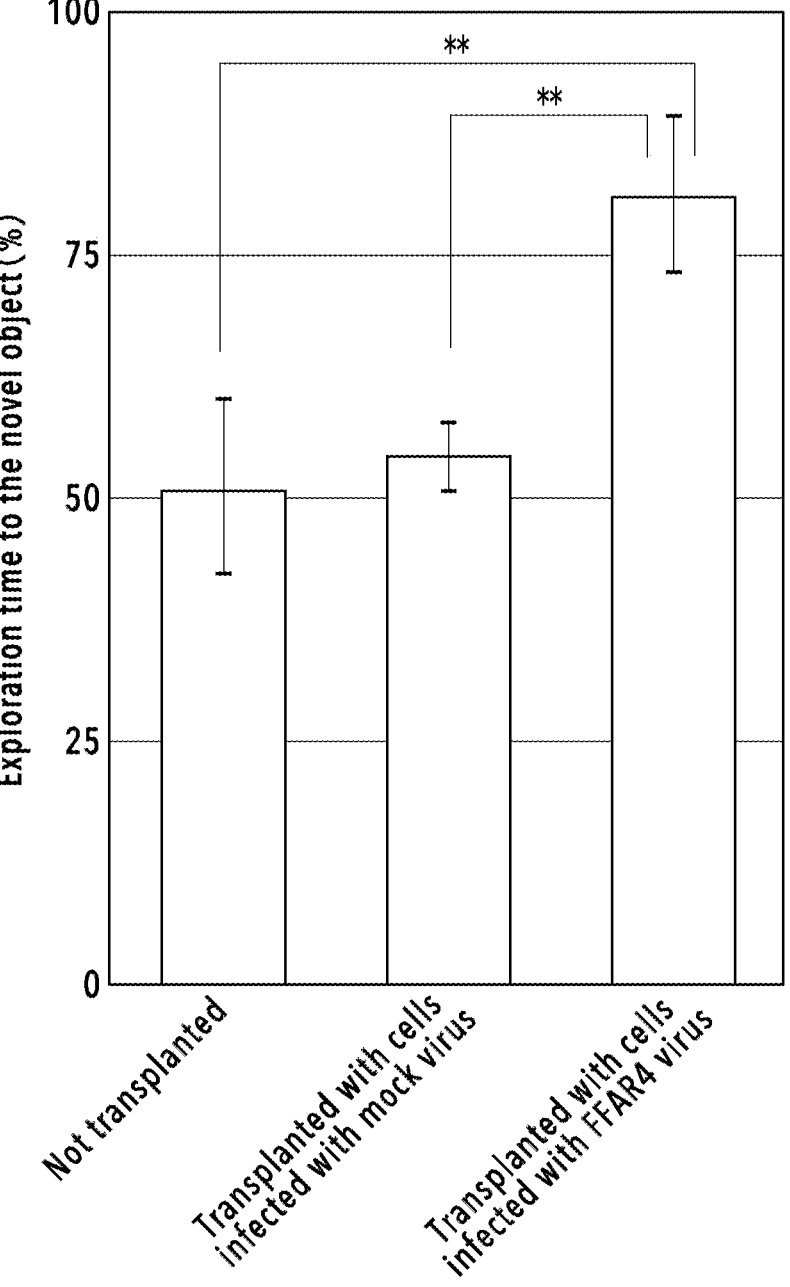
FIG. 14 shows results of the novel object recognition test in mice subcutaneously transplanted with adipose stem cells which were infected with FFAR4 virus, and then inducing differentiation thereto.

The results of the glucose tolerance test are shown in FIG. 12 and FIG. 13. In addition, the results of the novel object recognition test are shown in FIG. 14. In both of the novel object recognition test and the glucose tolerance test, significant improvement was observed in the mice transplanted with the cells infected with the FFAR4 virus.

INDUSTRIAL APPLICABILITY

The adipocytes over-expressing FFAR4 of the present invention can be used in treating or preventing various diseases, and particularly expected to treat or prevent a decrease in glucose tolerance and a decrease in cognitive ability associated with aging.

The invention claimed is:

1. A method for treating a decrease in cognitive ability associated with aging, comprising:

transplanting a transplant composition into a human or an animal, wherein the transplant composition comprises an adipocyte modified to express FFAR4 by introducing a gene encoding FFAR4 into the adipocyte, thereby treating the decrease in cognitive ability associated with aging.

2. The method according to claim 1, wherein the transplant composition contains an adipocyte obtained by forcibly expressing FFAR4 in an adipose stem cell or an adipose precursor cell collected from the human or the animal through gene introduction, and then inducing differentiation thereto to obtain an adipocyte.

3. The method of claim 1, wherein the adipocyte is obtained by a method comprising:

a) creating a chimeric gene in which a human FFAR4 cDNA is placed downstream of an appropriate promoter sequence;

b) introducing the chimeric gene into an adipose stem cell or an adipose precursor cell by incorporating the chimeric gene in a virus; and c) differentiating the adipose stem cell or the adipose precursor cell in which the chimeric gene has been introduced to adipocytes.

4. The method of claim 1, wherein the adipocyte is isolated from an adipose tissue of a transgenic mouse in which a gene encoding FFAR4 has been introduced.

5. A method for delaying a decrease in cognitive ability associated with aging, comprising:

transplanting a transplant composition into a human or an animal, wherein the transplant composition comprises an adipocyte modified to express FFAR4 by introducing a gene encoding FFAR4 into the adipocyte, thereby delaying the decrease in cognitive ability associated with aging.

6. The method of claim 5, wherein the adipocyte is obtained by a method comprising:

a) creating a chimeric gene in which a human FFAR4 cDNA is placed downstream of an appropriate promoter sequence;

b) introducing the chimeric gene into an adipose stem cell or an adipose precursor cell by incorporating the chimeric gene in a virus; and c) differentiating the adipose stem cell or the adipose precursor cell in which the chimeric gene has been introduced to adipocytes.

7. The method of claim 5, wherein the adipocyte is isolated from an adipose tissue of a transgenic mouse in which a gene encoding FFAR4 has been introduced.

* * * * *